(12) United States Patent
Taylor et al.

(10) Patent No.: US 12,279,861 B2
(45) Date of Patent: Apr. 22, 2025

(54) COLOR CHANGING DETECTION PATCH UTILIZING MICRONEEDLE SAMPLING OF INTERSTITIAL FLUID

(71) Applicant: UNM Rainforest Innovations, Albuquerque, NM (US)

(72) Inventors: Robert M Taylor, Albuquerque, NM (US); Justin T Baca, Albuquerque, NM (US)

(73) Assignee: UNM Rainforest Innovations, Albuquerque, NM (US)

( * ) Notice: Subject to any disclaimer, the term of this patent is extended or adjusted under 35 U.S.C. 154(b) by 824 days.

(21) Appl. No.: 17/274,866

(22) PCT Filed: Sep. 10, 2019

(86) PCT No.: PCT/US2019/050302
§ 371 (c)(1),
(2) Date: Mar. 10, 2021

(87) PCT Pub. No.: WO2020/055791
PCT Pub. Date: Mar. 19, 2020

(65) Prior Publication Data
US 2022/0047190 A1    Feb. 17, 2022

Related U.S. Application Data

(60) Provisional application No. 62/728,935, filed on Sep. 10, 2018.

(51) Int. Cl.
*A61B 5/145* (2006.01)
*A61B 5/00* (2006.01)
*A61B 10/00* (2006.01)

(52) U.S. Cl.
CPC ...... *A61B 5/14514* (2013.01); *A61B 5/14546* (2013.01); *A61B 5/4833* (2013.01);
(Continued)

(58) Field of Classification Search
CPC ............ A61B 5/14514; A61B 5/14546; A61B 5/4833; A61B 5/4845; A61B 5/6833;
(Continued)

(56) References Cited

U.S. PATENT DOCUMENTS 4,821,733 A * 4/1989 Peck ................ A61B 5/14521
600/362
5,203,327 A * 4/1993 Schoendorfer .... A61B 5/14521
600/362
(Continued)

FOREIGN PATENT DOCUMENTS

| CN | 108175415 A | 6/2018 |
|---|---|---|
| WO | 2017218878 A1 | 12/2017 |

OTHER PUBLICATIONS

Federal Institute of Industrial Property; International Search Report for PCT/US2019/050302; 2 pages; Dec. 19, 2019; Moscow RU.

*Primary Examiner* — David J. McCrosky
(74) *Attorney, Agent, or Firm* — Keith Vogt, Ltd.; Keith A. Vogt

(57) ABSTRACT

A wearable device that is applied to the skin of a user (e.g., patient), samples the user's interstitial fluid (IF), and indicates the presence or absence of a target substance. The device may further include a mechanism to ensure compliance and/or provide tamper resistance.

28 Claims, 3 Drawing Sheets

(52) U.S. Cl.
CPC .......... *A61B 5/4845* (2013.01); *A61B 5/6833* (2013.01); *A61B 5/685* (2013.01); *A61B 5/742* (2013.01); *A61B 2010/0006* (2013.01); *A61B 2010/0009* (2013.01); *A61B 2010/008* (2013.01); *A61B 2560/0412* (2013.01)

(58) Field of Classification Search
CPC . A61B 5/685; A61B 5/742; A61B 2010/0006; A61B 2010/0009; A61B 2010/008; A61B 5/1455; A61B 5/6832; A61B 5/68335; A61B 5/150969; A61B 2560/0412
See application file for complete search history.

(56) References Cited

U.S. PATENT DOCUMENTS

| | | | | |
|---|---|---|---|---|
| 6,169,915 | B1 * | 1/2001 | Krumbiegel | A61B 5/00 600/386 |
| 10,105,080 | B1 * | 10/2018 | Kam | A61B 5/14514 |
| 11,064,946 | B2 * | 7/2021 | Rogers | A61B 5/6898 |
| 2002/0138049 | A1 * | 9/2002 | Allen | A61N 1/303 264/219 |
| 2005/0245839 | A1 * | 11/2005 | Stivoric | A61B 10/0012 374/E1.004 |
| 2010/0256465 | A1 * | 10/2010 | Bernstein | A61B 5/743 600/576 |
| 2015/0282767 | A1 | 10/2015 | Stivoric et al. | |
| 2017/0188898 | A1 | 7/2017 | Jina et al. | |
| 2017/0340283 | A1 * | 11/2017 | Palaniappa | A61B 5/685 |

* cited by examiner

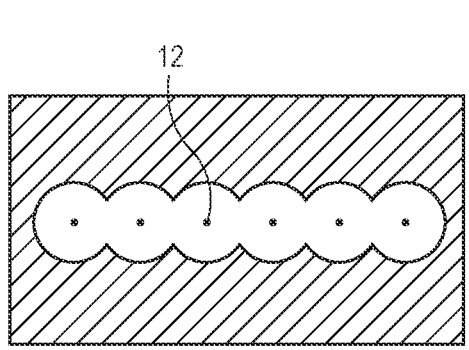
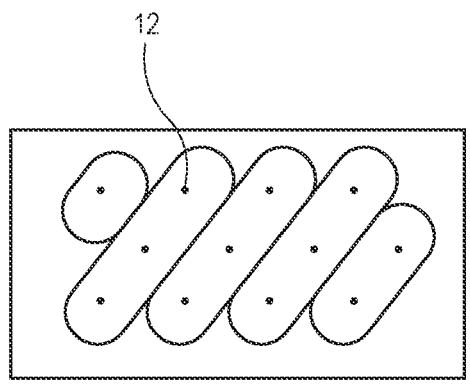
FIG. 4    FIG. 5
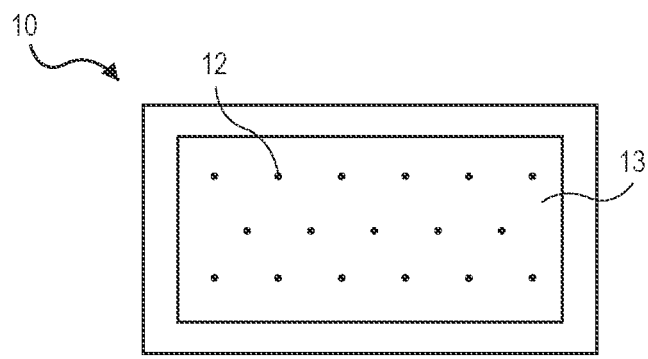
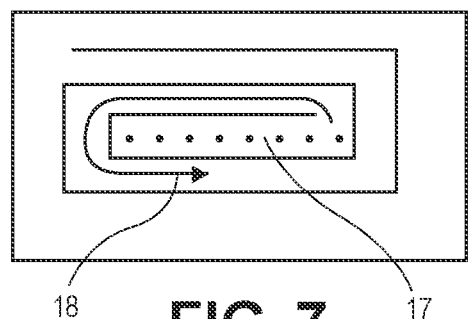
FIG. 6    FIG. 7

COLOR CHANGING DETECTION PATCH UTILIZING MICRONEEDLE SAMPLING OF INTERSTITIAL FLUID

CROSS-REFERENCE TO RELATED APPLICATIONS

The following application claims benefit of U.S. Provisional Application No. 62/728,935, filed Sep. 10, 2018, which is hereby incorporated by reference in its entirety.

BACKGROUND

There is a need for systems to detect and/or monitor alcohol or other substance consumption/use. In particular, there is a need for systems that enable the detection/monitoring of individuals who may be reticent or unable to self-report such consumption/use. Furthermore, there is a great need for systems that can detect any alcohol consumption, that cannot be altered or compromised by, for example, having someone else take the test, and which produce easy to understand and read results. Ideally, the system would enable immediate reading of results, eliminating the need for expensive laboratory tests and any concerns related to possible contamination or chain of custody issues that might stem or result therefrom.

SUMMARY

According to various embodiment the present disclosure provides a wearable device that is applied to the skin of a user (e.g., patient), samples the user's interstitial fluid (IF), and indicates the presence or absence of a target substance. The device may further include a mechanism to ensure compliance and/or provide tamper resistance.

BRIEF DESCRIPTION OF THE DRAWINGS

FIG. 4 is a bottom view schematic illustration of an alternate embodiment of an exemplary device according to the present disclosure.

FIG. 5 is a bottom view schematic illustration of another alternate embodiment of an exemplary device according to the present disclosure.

FIG. 6 is a top view schematic illustration of still another alternate embodiment of an exemplary device according to the present disclosure.

FIG. 7 is a top view schematic illustration of yet another alternate embodiment of an exemplary device according to the present disclosure.

DETAILED DESCRIPTION

Figure 1:
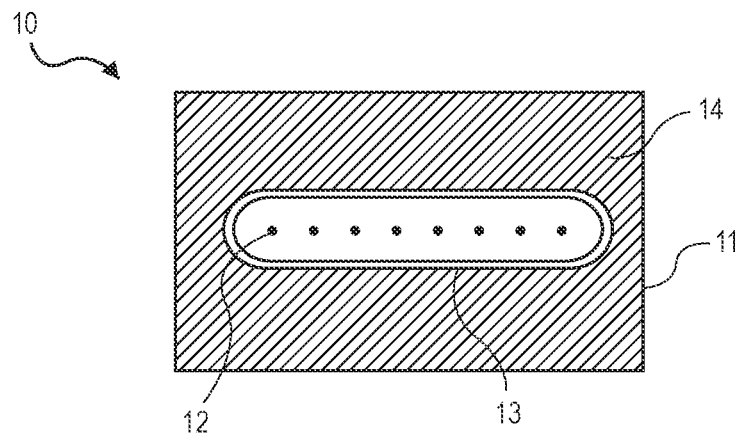
FIG. 1 is a bottom view schematic illustration of a of an exemplary device according to an embodiment of the present disclosure.

According to various embodiments the present disclosure provides a patch, swatch, or other wearable device that is applied to the skin of a user (e.g., patient), samples the user's interstitial fluid (IF), and indicates the presence or absence of a target substance. For the purposes of the present disclosure, the term "wearable" is intended to mean that the device is applied to the user's skin in such a manner that the user can go about daily activity for a certain amount of time while the device is performing its desired task without being hindered by the device. Examples of wearable devices under this definition include, for example, adhesive bandages, nicotine patches, and hormonal delivery patches (e.g., birth control patches). The device may be referred to herein interchangeably as a "device" or "patch," as the term "patch" is most commonly used to refer to such types of devices. However, no particular configuration, or embodiment should be specifically construed by the use of such terminology. According to various embodiments, the presently described device may sample the user's interstitial fluid to detect, for example, alcohol consumption, substance abuse, pharmaceutical clearance, and/or markers for a disease or other medical condition. According to various embodiments, the device indicates the presence or absence of a target substance which is associated with alcohol consumption, substance abuse, pharmaceutical clearance, and/or one or more medical conditions or diseases. Such indication may take the form of an easily identifiable visual marker such as, for example, a change of color the patch. Moreover, because it is anticipated that the presently described device may be used to test for the presence of one or more target substances that the user may not want to admit to having in their system (e.g., alcohol or prohibited substances), the presently described device may also include a mechanism for compliance insurance and/or tamper resistance. It should be noted for clarification that the term "user" in the present disclosure refers to the individual whose interstitial fluid is sampled by the presently described device even though the information provided by the device may, in fact, be directed, requested, or "used" by someone else including, for example, a doctor or other medical personnel, law enforcement officer, compliance officer, employer, guardian, etc.

According to various embodiments the device takes the form of a patch at least a portion of which adheres to the skin of the user. Those of skill in the art will be familiar with a variety of adhesives that may be used to apply such a medical device to a user's skin. According to some embodiments, the adhesive may be of a type that only enables a single application of the device such that if the device is removed, it cannot be reapplied to the same or a different user. Examples of adhesives may include, but are not limited to, single use glue-type adhesives that only allow the patch to stick to an individual once and will not re-stick if reapplication is attempted and single-use color change materials that change color based on body temperature when applied but lose color when removed and will not change color back.

According to various embodiments, the patch utilizes microneedles to sample the interstitial fluid. In general, the microneedles of the present device do not penetrate deep enough to hit nerves or blood supply. In experiments utilizing microneedles for other applications in humans, subjects report a pain response of 0-2 on a 1-10 pain scale (with 0 being no pain to 10 being severe pain).

Those of skill in the art will be familiar with a variety of microneedles that are useful for a variety of applications. In general, microneedles can be either solid or hollow. The present disclosure anticipates the use of either or both. According to some embodiments the needles, whether solid or hollow may be formed of a dissolvable material such as, though not necessarily limited to, a desiccated hydrogel.

As stated above, the present disclosure provides a wearable device that assays the wearer's interstitial fluid for the presence (or absence) of a target substance. Accordingly, the needles may include a coating that comprises one or more agents that directly or indirectly interact with the target substance in order to produce an indication of the presence or absence of such substance. Alternatively, in an embodiment that implements hollow needles, the needles may contain or be filled with a substance that comprises one or more agents that directly or indirectly interact with the target substance in order to produce an indication of the presence or absence of such substance.

According to a specific embodiment, the agent may be an enzyme which produces an enzymatic reaction when in the presence of the target substance. For example, if the end goal is to test for the presence of alcohol in the user's system, the agent may be alcohol dehydrogenase. According to this embodiment, if alcohol is present in the user's interstitial fluid, the alcohol will react with the alcohol dehydrogenase producing, for example, hydrogen peroxide as a bioproduct.

According to various embodiments, the device may include a mechanism which, when the target substance interacts with the agent, produces a detectable signal indicating the presence of the target substance. For example, in the embodiment described above, the hydrogen peroxide can then interact with a second agent to produce a visible color change. Of course, it will be understood that the detectable signal is not necessarily limited to a visible color change, but could instead, produce a visible symbol (similar to a plus or minus in a pregnancy test), or include some other communicable symbol. For example, the device may include mechanisms to communicate in either wired or wireless fashion with another device that can deliver the test results. Such mechanisms could be an electronic signal, a machine-readable physical symbol such as a bar code, serial number, QR code, etc., an RFID, or some other transmittable, scannable, active, or passive signal. Furthermore, such mechanisms and test results may or may not be visible to the user or may be only viewable upon application of some other mechanism. For example, the detectable signal may only be viewable under application of a certain frequency light including, but not limited to, ultraviolet (UV), black, or red light.

Of course, it will be understood that the present disclosure is not limited to only enzymatic reactions but may include other compounds or reactants that directly or indirectly react with the target substance. For example, other compounds that react with alcohol or alcohol metabolites include but are not limited to, Ethyl Glucuronide (EtG) or alcohol dehydrogenase.

Figure 2:
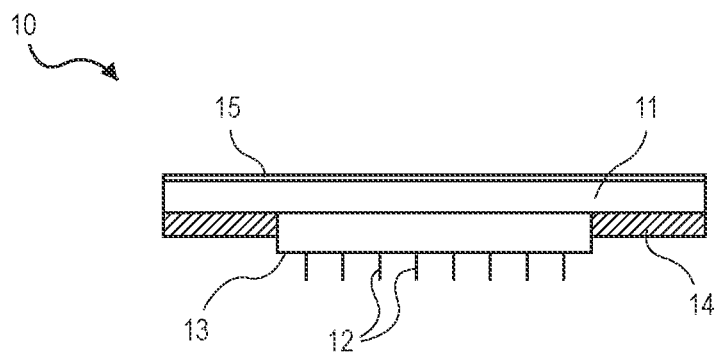
FIG. 2 is a side view of the device of FIG. 1.
Figure 3:
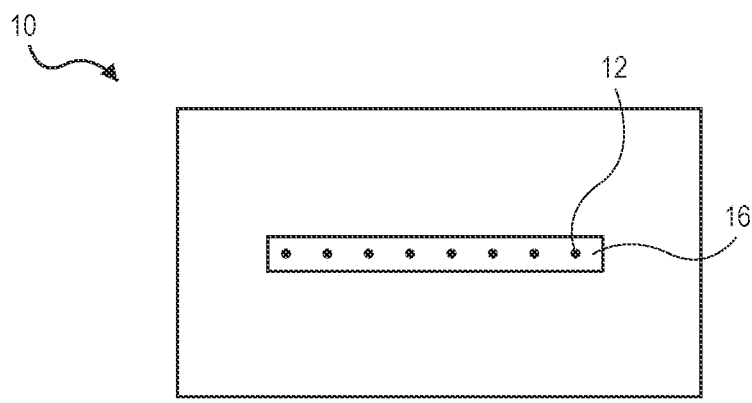
FIG. 3 is a top view of the device of FIG. 1.

FIGS. 1-3 show an exemplary device 10 according to an embodiment of the present disclosure. FIG. 1 is a bottom view of the device. As shown, this embodiment of the device includes a substrate 11 including a linear array of microneedles 12 surrounded by a needle guard 13. The substrate may be formed from one or more rigid or elastomeric materials including, for example, VisiJet M2 3D printing build materials. An elastomeric material may be more comfortable for the user and may enable greater freedom of movement. The bottom surface of the substrate is coated with an adhesive 14.

FIG. 2 is a side view of device 10, wherein the device includes the linear array of microneedles 12, needle guard 13, and adhesive 14. Substrate 11 which can be either attached to or contiguous with needle guard 13. Optionally, substrate 11 may further include a sealant layer 15.

FIG. 3 is a top view of device 10. As shown, substrate 11 includes a channel 16 in which microneedles 12 terminate. This channel may serve as a reservoir or include a paper strip or other assay material. According to some embodiments, this assay material can then absorb the interstitial fluid or components thereof for later analysis or may contain chromogens or other agents for immediate assay.

In use, the bottom surface of the device is applied to the user so that the microneedles 12 penetrate the outer dermis and sample the interstitial fluid. The sampled interstitial fluid travels to channel 16 via microneedles 12. As it travels, the interstitial fluid encounters the agent(s) and, if the target substance is present, the ensuing reaction produces a detectable signal. The signal may be, for example, but is not limited to, a detectable color. The signal may then, for example, be viewable in channel 16.

The device may include any number of microneedles as required to obtain or sample the appropriate amount of interstitial fluid for the particular assay or assays being performed. Accordingly, a variety of different configurations for the device may be used or desired. Exemplary alternate configurations are shown in FIGS. 4-7. However, it will be understood that configurations other than those specifically shown herein are also contemplated by the present disclosure.

FIG. 4 shows a bottom view of an alternate embodiment wherein the needles are surrounded by a non-linear needle guard.

FIG. 5 shows a bottom view of an alternative embodiment wherein the substrate includes a plurality of microneedle arrays.

FIG. 6 is a top view showing an alternate embodiment of a channel 16a wherein the channel has been expanded to cover most of the top surface area of the device.

FIG. 7 is a top view showing a further alternate embodiment wherein the channel incudes a central reservoir 17 with a long spiral channel 18 extending from the reservoir to promote fluid flow. Of course, it will be understood that myriad other channel configurations are possible including, but not limited to, zig zags, s-curves, columns, and various tortuous shapes.

While not shown, the device may be configured to test for more than one target substance and to provide different color or other indicators for each of the different target substances. Alternatively, or additionally, the device may be configured to produce different colors/indicators (or shades of colors/types of indicators) according to the concentration/amount of target substance found in the interstitial fluid. Moreover, it should be understood that the device may be configured to produce a detectable signal only when the target substance is not detected in the interstitial fluid (i.e. only in the absence of a particular target substance).

As stated above, the device may include one or more additional components that enforce or ensure compliance and/or tamper resistance while the patch is worn. In general, a compliance component will include at least a mechanism that ensures the device, or a portion thereof, has not been removed from the user and/or which provides an indication that the device has been removed even if the device is reapplied.

The compliance component may include, for example, a heat sensitive adhesive that changes color when the device is initially adhered to the user but that will lose its color if the patch is removed. This color change could take place only upon initial placement so that this particular change color would not be seen if the patch is reapplied to the same or a different individual.

Figure 8:
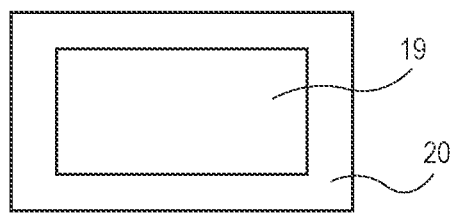
FIG. 8 is a schematic illustration of the visual indicator portion of an exemplary device according to the present disclosure prior to application to a user.
Figure 9:
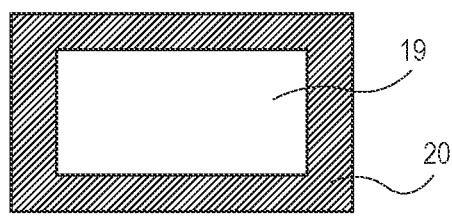
FIG. 9 is a schematic illustration the device of FIG. 8 after it has been properly applied and worn when no target substance is detected.
Figure 10:
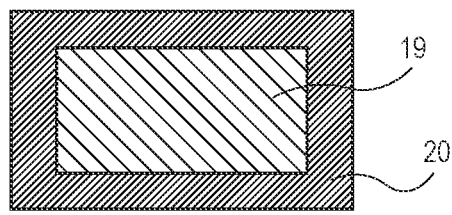
FIG. 10 is a schematic illustration the device of FIG. 8 after it has been properly applied and worn when target substance is detected.
Figure 11:
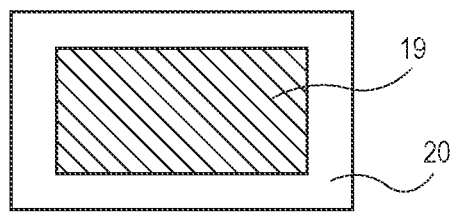
FIG. 11 is a schematic illustration the device of FIG. 8 after it has been removed and reapplied or otherwise tampered with and the target substance is detected.
Figure 12:
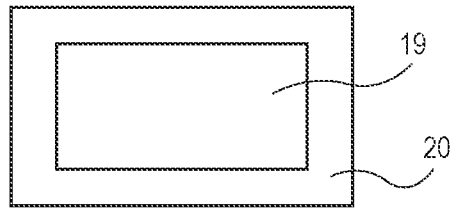
FIG. 12 is a schematic illustration the device of FIG. 8 after it has been removed and reapplied or otherwise tampered with and the target substance is not detected.

In FIGS. 8-12, a top view of a device including a compliance component as described above. The inner rectangle 19 delivers the results of the interstitial fluid assay (for example via a color change) while the outer rectangle 20 delivers the results of the compliance test. FIG. 8 shows the device prior to application where both the inner and outer rectangles are their "base" color. In FIG. 9, the device has been properly applied and worn (color change viewable in outer rectangle 20) and no target substance was detected in the user's interstitial fluid (no color change in inner rectangle 19). In FIG. 10, the device was properly applied and worn (color change in outer rectangle 20) and target substance is detected in the user's interstitial fluid (color change in inner rectangle 19). In FIG. 11, the device was removed and reapplied or otherwise tampered with (no color change in outer rectangle 20) and the target substance was detected in the user's interstitial fluid (color change in inner rectangle 19). In FIG. 12, the device was removed and reapplied or otherwise tampered with (no color change in outer rectangle 20) and target substance was not detected (no color change in inner rectangle 19).

Alternatively, or additionally, the patch may contain a "single application" adhesive that can only attach once. For example, the adhesive may be formulated in such a way that upon first application it initially attaches to the skin but wherein, when removed, the patch takes some epithelial cells along with it, thereby preventing the patch from attaching a second time.

According to another embodiment, the system may include a special marking, e.g., in the form of a stamp or something similar, that can be positioned (e.g., stamped) across both the patch and the adjacent exposed skin after the patch is initially applied. According to some embodiments, the stamp would be invisible unless visualized with one or more specific lights or agents. As a non-limiting example, the stamp could only be visible under UV or IR light. Alternatively, or additionally, the marking may be produced with an ink that includes an agent that is only visible after a counter-agent is swabbed over the ink. Examples of specific detection components may include, but are not limited to, an MRI contrast agent which is not readily available to the public and which is only detectable with a miniaturized NMR device such as nanoMR or DNAe), or through the use of an enzymatic reaction. In some cases, the stamp or marking may be made specifically for a specific court system, probation office, and/or business. Any number of markings/stamps in combination with any one or more of these methods could be employed to ensure the patch is not removed, reapplied, transferred to another individual, or otherwise compromised.

According to some embodiments, the system may include information related to the common and normal displacement of the patch due to exposure to water (e.g., from showering) or sweat (e.g., from exercising.)

According to some embodiments, the patch could include and release a harmless compound into the skin at a controlled release rate to provide information related to how long the patch had been worn. A color indicator or secondary swab, similar to the mechanism described above could enable detection of conditions such as, humidity, heat, ammonia, nitrate, ketosis, etc.

According to an embodiment, the patch may include a material such as, for example, cotton or other material, (similar to a nicotine or other type of patch) that holds the microneedles. A plastic or other waterproof, sweatproof, or durable "over-layer" may cover or overlay the material that holds the microneedles. According to an embodiment, the over-layer may include a waterproof, sweatproof, durable adhesive that may only be able to stick (be applied) once. Moreover, the patch may have an adhesive, stitch, glue, barrier, writing, printing, or other mechanism that prevent the inner material holding the microneedles from being taken out and replaced with a new one.

According to various embodiments, the device described herein can be used to obtain immediate or almost immediate test results or to test for exposure to or use of specific substances over a period of time. For example, the device could be used in a hospital setting to determine whether a specific target substance (desirable or undesirable) is in the user's system. Alternatively, the device could be used instead of or in addition to breathalyzer or other tests to determine whether a user is currently inebriated or under the influence of a particular substance. In this case, the device may be applied for only of a few minutes or hours. Alternatively, the device may be worn for longer amounts of time, for example, between 1-24 hours or between 1-30 days, in order to monitor whether the user is complying with particular requirement either to take or abstain from certain medications, alcohol, or other substances. For example, an inmate could be required to wear the device during incarceration, a parolee could be required to wear the device between meetings with a parole officer, an employee could be required to wear the device during work hours, or a patient could be required to wear the device while in the hospital or between doctor's visits.

Accordingly, the disclosed device could be useful to law enforcement, probation courts, family courts, restraining order enforcement, DWI offenses, businesses and companies that require random testing or have a strict no alcohol/drug use policy, national labs, and also to industries such as manufacturing and work plants. For instance, a company might save money on insurance premiums if their employees wear the device when they get to the job site or plant and take it off when they leave. If an accident occurs on the job, the employer would have proof that no alcohol was in the system of the employee. Moreover, as explained above, the described herein is not limited to alcohol detection but could be designed in a similar fashion to detect other substances of abuse such as, but not limited to, marijuana, opiates, cocaine, pcp, and others. Accordingly, it will be understood that the specific mechanisms of the system/patch described herein could be tailored to the specific use and requirements of any of these industries.

Furthermore, the device described herein is not limited to alcohol or drugs of abuse, but could also be utilized in, for example, hospitals, emergency rooms, clinics, care facilities, as well as for home use. For example, a device could be worn to ensure, detect, and signify when a prescribed pharmaceutical or other agent has been eliminated from a patient's body, thus signaling that a physician could prescribe or inject a different, possibly interacting pharmaceutical or treatment regime. Alternatively, the device could be used to ensure or monitor whether a user is maintaining a specific drug regimen. This might be particularly helpful for patients or care givers who have trouble remembering to take medications or who do not want to take medications or for whom very specific levels must or should be maintained. Patients who are very young, unconscious, or otherwise unable to monitor or communicate their medication levels would particularly benefit from this device.

According to yet another embodiment, the device may be configured to diagnose specific diseases or conditions and follow treatment outcomes. For instance, Diabetic ketoacidosis (DKA) is one of the most dangerous complications of diabetes. DKA is also a complication of diabetes with the highest mortality rates with 25%-40% of children with undiagnosed Type-I diabetes presenting with DKA. This can often lead to cerebral edema which accounts for 50%-85% of deaths in children with Type-I diabetes. Additionally, a 30% increase in DKA incidence has been documented over the past decade. Moreover, 15%-20% of adult and 30%-40% of adolescent diabetic patients, with undiagnosed diabetes, first present with DKA. Characteristics of DKA are decreased secretion of insulin, leading to hyperglycemia and increased production of toxic ketone bodies. In the emergency room (ER), DKA is often diagnosed as glucose levels less than 13.9 mmol/L, pH less than 7.3, serum bicarbonate less than 18 mmol/L, anion gap less than 10, and positive urine and serum ketones. Blood sampling, for ketones, typically tests for β-hydroxy-butyrate (BHB), which is the predominant ketone species found in blood. Urine sampling, for ketones, tests for acetoacetate, which is the predominant ketone species found in urine. Blood testing is invasive and, due to its superb buffering ability, systemic blood pH changes slowly. Urine testing is least invasive but, due to filtering in the kidneys and normal biological processes, it takes biomarkers longer to be detected. Earlier diagnosis, treatment, and management of DKA are of vital importance to enhance better patient outcomes.

Interstitial fluid has a much lower buffering capacity compared with blood, due to lower levels of buffering agents such as hemoglobin and albumin. Normal blood and interstitial fluid pH are 7.35-7.45 and 6.6-7.6, respectively. Due to its lowered buffering capacity, interstitial fluid can have changes in pH that are greater than, and develop more rapidly than, that of blood. Therefore, interstitial fluid pH level changes may happen more rapidly and be a better, faster diagnostic of potential ketoacidosis than blood or urine. Additionally, it has been shown that interstitial fluid levels of substances, such as glucose and lactate, differ when compared to blood and also change concentrations at different rates. Testing interstitial fluid for molecular changes that are important in the development of DKA, such as glucose, lactate, pH, and ketone bodies could prove beneficial for earlier detection, better treatment, and faster, better outcomes for patients presenting with DKA.

Accordingly, in one exemplary embodiment, patients admitted to the ER with DKA could have a device of the present disclosure applied. The device could be configured, for example, such that at least of portion of the device turns red to show the ketone levels are high and which, over time, changes to green when ketones have decreased. This would signal that the treatment course was working and limit the number of invasive blood draws that would be needed.

The terms and expressions that have been employed are used as terms of description and not of limitation, and there is no intent in the use of such terms and expressions to exclude any equivalent of the features shown and described or portions thereof, but it is recognized that various modifications are possible within the scope of the invention as claimed. Thus, it will be understood that although the present invention has been specifically disclosed by preferred embodiments and optional features, modification and variation of the concepts herein disclosed may be resorted to by those skilled in the art, and that such modifications and variations are considered to be within the scope of this invention as defined by the appended claims.

All patents and publications referenced below and/or mentioned herein are indicative of the levels of skill of those skilled in the art to which the invention pertains, and each such referenced patent or publication is hereby incorporated by reference to the same extent as if it had been incorporated by reference in its entirety individually or set forth herein in its entirety. Applicants reserve the right to physically incorporate into this specification any and all materials and information from any such cited patents or publications.

What is claimed is:

1. A wearable device comprising:
   microneedles for sampling the interstitial fluid of a user while the device is applied to the user's skin;
   a mechanism for detecting the presence or absence of a target substance in the sampled interstitial fluid;
   a signaling mechanism for indicating whether or not the target substance was detected in the sampled interstitial fluid; and
   a compliance component including an indicator that indicates whether the device has been removed even if the device has been reapplied, wherein the indicator is a portion of the device that undergoes a color change when the device is applied to the user's skin; and
   wherein the indicator is visible to the user.

2. The wearable device of claim 1 wherein the signaling mechanism includes a color changing component that indicates the presence or absence of the target substance.

3. The wearable device of claim 2 wherein the color changing component provides an indication of the concentration of the target substance in the interstitial fluid.

4. The wearable device of claim 1 wherein the device compliance component provides an indication of how long the device has been worn by the user.

5. The wearable device of claim 1 wherein the target substance is alcohol and the device indicates whether the user has consumed alcohol.

6. The wearable device of claim 1 wherein the device comprises an indicator that indicates whether the user has eliminated a specific pharmaceutical substance from their system.

7. The wearable device of claim 1 wherein the target substance is an indicator of diabetic ketoacidosis.

8. The wearable device of claim 7 wherein the target substance is a ketone.

9. The wearable device of claim 1 wherein the device comprises a needle guard surrounding the microneedles.

10. The wearable device of claim 9 wherein the needle guard is non-linear.

11. The wearable device of claim 9 wherein the device comprises a substrate including a linear array of the microneedles surrounded by the needle guard.

12. A wearable device comprising:
   microneedles for sampling the interstitial fluid of a user while the device is applied to the user's skin;
   a mechanism for detecting the presence or absence of a target substance in the sampled interstitial fluid;
   a signaling mechanism for indicating whether or not the target substance was detected in the sampled interstitial fluid; and
   a compliance component including an indicator that indicates whether the device has been removed even if the device has been reapplied, wherein the compliance component comprises a stamp or marking that covers a portion of the device and extends onto the user's skin; and wherein the stamp or marking is only viewable upon application of a secondary mechanism.

13. The wearable device of claim 12 wherein the secondary mechanism is light in a specific wavelength.

14. The wearable device of claim 12 wherein the secondary mechanism is a substance for being applied to the device and/or skin.

15. The wearable device of claim 12 wherein the compliance component comprises a stamp or marking that covers a portion of the device and extends onto the user's skin.

16. The wearable device of claim 12 wherein the secondary mechanism is light in a specific wavelength.

17. The wearable device of claim 12 wherein the signaling mechanism includes a color changing component that indicates the presence of absence of the target substance.

18. The wearable device of claim 12 wherein the color changing component provides an indication of the concentration of the target substance in the interstitial fluid.

19. The wearable device of claim 12 wherein the device compliance component provides an indication of how long the device has been worn by the user.

20. The wearable device of claim 12 wherein the target substance is alcohol and the device indicates whether the user has consumed alcohol.

21. The wearable device of claim 12 wherein the target substance is a substance of abuse and the device indicates whether the user has a substance of abuse in their system.

22. The wearable device of claim 12 wherein the device comprises an indicator that indicates whether the user has eliminated a specific pharmaceutical or other agent target substance from their system.

23. The wearable device of claim 12 wherein the target substance is an indicator of diabetic ketoacidosis.

24. The wearable device of claim 23 wherein the target substance is a ketone.

25. The wearable device of claim 12 wherein the device comprises a needle guard surrounding the microneedles.

26. The wearable device of claim 12 wherein the needle guard is non-linear.

27. The wearable device of claim 26 wherein the device comprises a substrate including a linear array of the microneedles surrounded by the needle guard.

28. A wearable device comprising:
   microneedles for sampling the interstitial fluid of a user while the device is applied to the user's skin;
   a mechanism for detecting the presence or absence of a target substance in the sampled interstitial fluid;
   a signaling mechanism for indicating whether or not the target substance was detected in the sampled interstitial fluid;
   a compliance component including an indicator that indicates whether the device has been removed even if the device has been reapplied, wherein the indicator is visible to a user and said indicator is a portion of the device that undergoes a color change when the device is applied to the user's skin; and
   wherein the color only takers place upon initial placement of the device and reverts to the original color if the device is removed from the user's skin and the device will not undergo another color change even if reapplied to the user or another user's skin.

* * * * *